United States Patent
Patois et al.

(10) Patent No.: US 6,395,927 B1
(45) Date of Patent: May 28, 2002

(54) METHOD FOR PREPARING ACETIC ACID AND/OR METHYL ACETATE BY ISOMERIZATION AND CARBONYLATION

(75) Inventors: Carl Patois, Riedisheim; Robert Perron, Charly; Daniel Thiebaut, Billere, all of (FR)

(73) Assignee: Acetex Chimie, Paris (FR)

( * ) Notice: Subject to any disclaimer, the term of this patent is extended or adjusted under 35 U.S.C. 154(b) by 0 days.

(21) Appl. No.: 09/142,175

(22) PCT Filed: Mar. 27, 1997

(86) PCT No.: PCT/FR97/00551

§ 371 (c)(1),
(2), (4) Date: Sep. 23, 1998

(87) PCT Pub. No.: WO97/35828

PCT Pub. Date: Oct. 2, 1997

(30) Foreign Application Priority Data

Mar. 27, 1996 (FR) .............................. 96 03781
Jul. 10, 1996 (FR) .............................. 96 08590

(51) Int. Cl.[7] ........................ C07C 51/10; C07C 53/08
(52) U.S. Cl. ...................... 562/517; 562/518; 562/519; 562/607; 560/232
(58) Field of Search .................. 560/232; 562/517, 562/518, 519, 607

(56) References Cited

U.S. PATENT DOCUMENTS 4,613,694 A * 9/1986 Ray
5,723,660 A * 3/1998 Morimoto et al.
5,847,204 A * 12/1998 Nobel
5,883,295 A * 3/1999 Sunley et al.

* cited by examiner

Primary Examiner—Gary Geist
Assistant Examiner—Robert W. Deemie
(74) Attorney, Agent, or Firm—Dennison, Scheiner & Schultz

(57) ABSTRACT

A method for preparing acetic acid and/or methyl acetate by simultaneous isomerization and carbonylation reactions. A reaction mixture is provided containing at least one reagent which provides formyl radicals and at least one further reagent which provides methyl radicals, together with water in an amount of at most 5% by weight, carbon monoxide at a partial pressure between $0.1 \cdot 10^5$ Pa and $25 \cdot 10^5$ Pa, a solvent and a catalytic system which contains at least one halogenated promoter and at least one iridium-based compound. In a typical reaction mixture, methyl formate is isomerized to form acetic acid according to the reaction:

$$HCOOCH_3 \rightarrow CH_3COOH$$

while methanol undergoes carbonylation to form acetic acid according to the reaction:

$$CH_3OH + CO \rightarrow CH_3COOH$$

The reagent which provides the formyl radicals is kept at or below 20% by weight of the reaction mixture, while the molar ratio of methyl radicals to formyl radicals in the mixture is greater than 1.

32 Claims, No Drawings

METHOD FOR PREPARING ACETIC ACID AND/OR METHYL ACETATE BY ISOMERIZATION AND CARBONYLATION

BACKGROUND OF THE INVENTION

The object of the present invention is the preparation of acetic acid and/or methyl acetate, by using an isomerisation reaction and a carbonylation reaction.

Various means of access to acetic acid are known and used industrially. Amongst these is the carbonylation reaction of methanol. This carbonylation reaction may notably be carried out in the liquid phase, under the pressure of carbon monoxide, which is one of the reagents, in the presence of a homogeneous catalytic system comprising a compound based on rhodium and/or iridium and an iodinated promoter.

Another means of access is constituted by the isomerisation reaction of methyl formate in the presence of a catalyst based on rhodium or iridium.

The known iridium-catalysed isomerisation methods are carried out under a nitrogen atmosphere. It has in fact been noted that the carbon monoxide did not bring about any particular advantage during the reaction and could even be the cause of a certain inhibition of the isomerisation reaction, it favouring side reactions. It is to be noted that such a behaviour is entirely different from that which is observed when the catalytic system is rhodium-based, in which case the presence of carbon monoxide is essential for keeping the metal in the homogeneous phase. This iridium-catalysed type of method, whose interest is not questioned here, does not have any real interest industrially since the reaction which is described therein is not sufficiently efficient. In fact, the reaction rates are only in the order of 2 mol/h/l of acid and/or ester produced.

It has been proposed, in order to improve the results of the above-mentioned method, to use the isomerisation reaction in the presence of a strong acid of the sulphonic acid type, such as paratoluenesulphonic acid for example. Under the conditions of this method, the reaction is carried out using significant amounts of methyl formate to be isomerised, which is consequently also used as solvent for the reaction. If this improvement contributes to the improvement of the activity of the reaction, it does nevertheless have the disadvantage of necessitating the use of a further compound, which does not simplify the method.

Further, it is possible that this acid degrades under the conditions of the composition of the reaction medium and its use.

SUMMARY OF THE INVENTION

An aim of the present invention is to propose a method of preparation of acetic acid and/or methyl acetate in carrying out simultaneously an isomerisation reaction of methyl formate and a carbonylation reaction of a reagent which provides a methyl radical, such as methanol for example.

Such a method has the advantage of softening the functioning conditions of the isomerisation method or even of that of carbonylation.

In fact, it is possible to use commercial methyl formate, i. e. that contains up to a few percent of methanol, and it is noted that the presence of this alcohol brings about its contribution to the production of acetic acid and/or the corresponding ester. Furthermore, the possibility of carrying out the isomerisation of methyl formate may enable increasing the capacity of production of an installation of methanol carbonylation, without taking on the high investments necessary for increasing the production of carbon monoxide which is one of the reagents employed for this reaction.

Furthermore, and whether it be in one or the other above cases, to bring about a diversification of the reagents is an advantage which is well understandable.

It is entirely remarkable that, despite implementation conditions which are not a priori favourable to it, the carbonylation reaction takes place with a good productivity.

These and other goals are met by the present invention which has therefore for object the preparation of acetic acid and/or methyl acetate, by reaction of reagents which provide formyl radicals and reagents which provide methyl radicals, in the presence of carbon monoxide, water, a solvent and a catalytic system comprising at least one halogenated promoter and at least one iridium-based compound. According to this method, a partial carbon monoxide pressure is kept between $0.1 \cdot 10^5$ Pa and $25 \cdot 10^5$ Pa, and an amount of reagents which provide the formyl radicals of below or equal to 20% by weight of the reaction mixture, and the reagents which provide the methyl and formyl radicals are fed in in a molar ratio of methyl radicals to the formyl radicals of greater than 1.

The above conditions enable simultaneously carrying out the isomerisation of the ester coming from the formyl radicals and the carbonylation of the methyl radicals fed in.

It has in fact been noted, on the contrary to what was asserted in the prior art, that the presence of carbon monoxide was essential for the isomerisation reaction of the ester in the presence of iridium.

Furthermore, the carbon monoxide is consumed and intervenes as reagent in the carbonylation reactor.

According to the second characteristic above, the content of reagent providing the formyl radicals is kept at lower than 20% by weight of the reaction mixture.

Furthermore, the ratio of the methyl radicals to the formyl radicals enables determining the nature of the reaction(s) which are carried out during the method. In fact, when this ratio is equal to 1, only the isomerisation reaction is carried out and this leaves the context of the present invention, whereas if this ratio is greater than 1, both the isomerisation and carbonylation reactions take place.

DETAILED DESCRIPTION OF THE INVENTION

The method of the invention is carried out in the presence of a catalytic system which comprises at least one halogenated promoter and at least one iridium-based compound.

The halogenated promoter, which represents one of the constituents of the catalytic system, is selected preferably from iodinated compounds.

The halogenated promoter may be in the form of iodine, alone or in combination with other elements such as for example hydrogen, a $C_1$–$C_{10}$ alkyl radical, a $C_1$–$C_{10}$ acyl radical, or even alkali metal iodides or metal iodides, such as transition metal iodides, or iodides of metals of column IIA of the periodic classification of the elements.

It is to be noted that the halogenated promoter may be constituted of a mixture of several of the above-mentioned promoters.

The context of the present invention shall not be left in preparing said alogenated promoters in situ with the aid of appropriate precursors.

According to a particularly advantageous embodiment of the invention, the halogenated promoter is selected from iodine, hydroiodic acid, methyl iodide, aluminium iodide, chromium iodide, lithium iodide, potassium iodide; these compounds being used alone or as mixtures. Preferably, the halogenated promoter comprises iodine and a methyl-type radical.

Furthermore, the amount of halogenated promoter kept during the reaction is more particularly between 0.1 and 20% by weight of the reaction mixture. Preferably, the halogenated promoter content is between 1 and 15% by weight of the reaction mixture.

It is to be noted that the amounts of promoter indicated above are given as an indication. In fact, the person skilled in the art has even to find the optimal compromise between, on the one hand, a maximal efficiency of this compound, which has a beneficial effect on the activity and the stability of the catalyst, and on the other hand, economical considerations linked to the cost engaged in the recycling of this compound in the method.

The second element of the catalytic system used in the method according to the invention is constituted by at least one iridium-based compound.

First of all, the reaction according to the invention is more particularly carried out in the presence of a homogeneous catalyst. In other words, this signifies that the iridium-based compound is notably in a form which is soluble in the reaction mixture. It is to be noted that the presence of a part of said iridiumbased compound in a non-dissolved form does not present any major difficulty for the implementation of the reaction.

All the iridium compounds which are soluble or able to be dissolved in the reaction medium, under the conditions of implementation of the invention, may be used. As examples, and without intending to be limiting, metallic iridium, its simple salts, its oxides or even its co-ordination complexes may notably be appropriate in the implementation of the invention.

As simple iridium salts, the iridium halides are conventionally used. The halogen is most particularly selected from chlorine, bromine and iodine, the latter being preferred. Thus, compounds such as $IrI_3$, $IrBr_3$, $IrCl_3$, $IrI_3 \cdot 4H_2O$, $IrI_4$, $IrBr_3 \cdot 4H_2O$ may be used in the method according to the invention.

Oxides selected from $IrO_2$, $Ir_2O_3 \cdot xH_2O$ may equally be conveniently used in the method according to the invention.

Regarding the soluble co-ordination complexes of iridium, the compounds which are most commonly used are those having ligands selected from carbon monoxide, or a carbon monoxide/halogen combination, the halogen being selected from chlorine, bromine or more particularly iodine. It is not nevertheless excluded to use soluble iridium complexes whose ligands are selected from the organophosphorus compounds and organo-nitrogen compounds for example.

As co-ordination complexes known to the person skilled in the art which are particularly convenient in the implementation of the invention, $Ir_4(CO)_{12}$, $Ir(CO)_2I_2^-Q^+$, $Ir(CO)_2Br_2^- Q^+$, $Ir(CO)_2Cl_2^- Q^+$, may be cited without intention to limit; in which formulae Q may be notably hydrogen, an $NR_4$ group, or a $PR_4$ group with R selected from hydrogen or a hydrocarbon radical.

These catalysts may be obtained by any method known to those skilled in the art. Thus, the EP 657 386 and WO 95/17963 patents may be referred to for the preparation of iridium-based catalytic solutions which are appropriate for the implementation of the present invention.

It is to be noted that the reaction according to the invention may be carried out with a catalytic system which comprises, besides iridium, one or more other metals from Group VIII. More particularly, the reaction may be carried out with an association of rhodium and iridium, or even an association of ruthenium and iridium, or an association of rhenium and iridium, or even a catalytic system based on any combination of these four metals.

If such a variant is adopted, the molar ratio of iridium to the other associated metals is more particularly between 1/10 and 10/1. Preferably, it is greater than 1/1.

Generally, the total iridium concentration in the reaction medium is between 0.1 and 100 mmol/l preferably between 1 and 25 mmol/l.

As has been mentioned previously, the reaction is carried out by feeding in reagents which provide formyl radicals and methyl radicals.

<<Reagents providing formyl radicals >>, refers to reagents of formula HC(O)OR in which formula R represents a hydrogen atom or a methyl group. According to a particular embodiment of the invention, methyl formate is fed in, with the proviso that it is not of course excluded to feed in formic acid or a mixture of acid and ester.

By <<reagents providing methyl radicals >>, reagents are defined of formula $CH_3$—R', in which —R' represents —OH, —$OCH_3$, —OC(O)$CH_3$, —OC(O)H. Here again, the context of the invention shall not be left in feeding in several reagents which provide the above-mentioned methyl radicals.

It is to be noted that in the case of methyl formate, the molecule introduced consists of both a methyl radical and a formyl radical. In this case, the molecule comprises each one of the two radicals.

It is also to be noted that, in the case where the reaction is fed with dimethyl ether, $CH_3$—O—$CH_3$, the molecule introduced consists of two methyl radicals.

<<Methyl and formyl radicals fed into the reaction >> is understood as meaning the methyl and formyl radicals consumed by this reaction. Thus, recycled methyl and formyl radicals are not included if the method is carried out continuously, or even the radicals remaining in the reaction medium at the end of the reaction if it is conducted discontinuously.

As it has been mentioned before, the reaction is carried out by feeding in the methyl and formyl radicals in a molar ratio which is greater than 1.

The value of this ratio enables fixing the reactions which are carried out.

The fact that this ratio be greater than 1 renders the conditions favourable for the existence of both the isomerisation reaction and the carbonylation reaction.

The molar ratio of the methyl radicals to the formyl radicals may vary within large limits. It may thus be between 1 and 100. According to a particular embodiment of the invention, the above-mentioned molar ratio is between 1 (excluded) and 20 (included).

The isomerisation reaction and carbonylation reaction according to the invention is carried out in the presence of water and a solvent.

More particularly, the amount of water expressed by weight of the reaction mixture, varies between 0 (excluded) and 5%. Advantageously, said content is between 0 (excluded) and 2% by weight.

It is to be noted that the water plays an important role in the method. In fact, it participates in keeping the catalyst in solution, particularly in the partial vaporisation (flash) zone of the mixture which shall be described later. It also enables limiting the side-reactions known for the methods carried out under anhydrous conditions.

Regarding the solvent, it may comprise one or more carboxylic acids as well as other compounds designated co-solvents in the present text.

According to a particular embodiment of the present invention, the carboxylic acid is selected from the aliphatic acids having from 2 to 10 carbon atoms, preferably from 2 to 5 carbon atoms. According to a particularly advantageous embodiment of the present invention, said carboxylic acid is acetic acid. The context of the present invention shall not be left in employing a mixture of the above-mentioned acids.

According to another possibility, the solvent may further comprise formic acid, which is nevertheless counted as a carboxylic acid.

The context of the present invention would not of course be left in using a additional solvent (co-solvent) inert under the reaction conditions. As an example of this type of solvent, esters, ethers, ketones, amides, sulphoxides or even hydrocarbons may be cited. The preferred co-solvent is the ester of the acid produced, i. e. methyl acetate.

Thus, a particularly advantageous variant of the invention consists in using, as solvent, a mixture comprising the acid produced, optionally the corresponding ester of the acid produced, and formic acid.

The amount of solvent used in the reaction corresponds to making up 100% by weight of the reaction mixture.

If one or more co-solvents are employed, the amount of carboxylic acid is preferably greater than that of the co-solvent. Thus, in the case where the cosolvent is methyl acetate, the weight content of it is preferably lower than or equal to that of acetic acid.

According to a particular embodiment of the invention, the amount of formic acid present in the reaction medium is kept below 15% by weight of the reaction mixture. Preferably, the formic acid content is kept below 12% and more particularly below 10% by weight of the reaction mixture.

Furthermore, according to an advantageous embodiment of the present invention, the amount of free carboxylic acids present in the reaction mixture is greater than 25% by weight of said mixture and such that the whole of the constituents of the reaction mixture represents 100% by weight of the reaction mixture. More particularly, the free carboxylic acids content is greater than 30% by weight of the reaction mixture and preferably is greater than 40% by weight of the reaction mixture.

It is to be noted that the formic acid/methyl acetate molar ratio may be different from 1 under the conditions of the reaction, i. e. greater than or lower than this value. The reaction may obviously be carried out with a molar ratio equal to 1.

The method of the invention therefore consists in maintaining a specific partial carbon monoxide pressure and a specific concentration of reagent which provides the formyl radicals during the reaction.

Thus, the partial carbon monoxide pressure is kept between $0.1·10^5$ Pa and $25·10^5$ Pa.

The pressures are expressed in absolute Pascals, and have been measured in the hot, i.e. under the conditions of the temperature of the reaction.

According to a more particular embodiment of the invention, a partial carbon monoxide pressure is kept at $0.5·10^5$ Pa, and preferably greater than $10^5$ Pa.

The partial carbon monoxide pressure is advantageously below $15·10^5$ Pa. More particularly, it is lower than $10·10^5$ Pa.

When the conditions are favourable both for the isomerisation reaction and that of carbonylation, it is noticed that there is a consumption of this gas due to the carbonylation reaction, this consumption is necessary to compensate for the conservation of the partial carbon monoxide pressure within the above-mentioned ranges required.

It is to be noted that the carbon monoxide can be used in the pure form or diluted in gases such as hydrogen, methane, carbon dioxide or any other type of gas such as nitrogen for example. Preferably, carbon monoxide which is at least 98% pure by volume is used.

According to a characteristic of the present invention, the content of the reagent providing formyl radicals is kept below 20% by weight of the reaction mixture.

Preferably, the above-mentioned reagent content does not go over 10% by weight of the reaction mixture. According to a particularly advantageous embodiment of the present invention, the above-mentioned reagent content does not go over 5% by weight of the reaction mixture.

When the reaction is carried out continuously, the above-mentioned characteristics are preferably kept constant throughout the reaction, but an evolution of the partial carbon monoxide pressure is possible during the reaction, insofar as it is always found within the above-mentioned range.

When the reaction is carried out discontinuously, the amount of reagent which provides the formyl radicals is kept below the values indicated although going down, since said reagent is consumed by the reaction. As for the partial carbon monoxide pressure, it may or may not be kept constant, provided that it is found within the range of above-mentioned values.

The reaction is generally carried out at a temperature between 150 and 250° C. More particularly, the reaction temperature is between 175 and 210° C. Preferably, it is between 175 and 200° C.

The total pressure under which the reaction is carried out is generally greater than atmospheric pressure. More particularly, it is lower than $100·10^5$ Pa and preferably lower than or equal to $50·10^5$ Pa. The pressures are expressed in absolute Pascals, and are measured in the hot, i.e. under the conditions of temperature of the reaction.

The isomerisation and carbonylation reaction being the object of the invention is preferably carried out in the presence of a corrosive metals content of lower than 2,000 ppm. The corrosive metals are especially iron, nickel, chromium, molybdenum, and optionally zirconium. The corrosive metals content in the reaction mixture is maintained by the methods known to the person skilled in the art, such as for example, selective precipitation, liquid extraction, passing through ion exchange resins.

The reaction is carried out in apparatuses which are resistant to the corrosion created by the medium. Thus, zirconium or even alloys of the Hastelloy® C or B type are particularly convenient under the conditions of carrying out the reaction.

During the starting up of the reaction, the various components are introduced into an appropriate reactor, equipped with means of stirring in order to ensure a good homogeneity of the reaction mixture. It is to be noted that if the reactor comprises preferably a mechanical means of stirring the reaction mixture, it is not excluded to operate without such means, it being possible for the homogenisation of the mixture to be effected by the introduction of the carbon monoxide into the reactor.

It is to be noted that the reaction may be conveniently carried out in a reactor of the piston type.

The combination of several reactors of the stirring and piston types is of course envisagable.

The introduction of carbon monoxide can take place directly in the reactor wherein the reaction according to the invention takes place, but also in the recycling zone which will be described further on.

The reaction mixture leaving the reactor is treated in an appropriate manner in order to separate the products of the reaction mixture which notably comprise the catalyst.

For this, and in the case of carrying out the reaction continuously, a conventional technique may be employed for example which consists in expanding the mixture in a way so as to cause a partial vaporisation of the latter. This operation is carried out using a valve which enables expanding the mixture, the latter being then introduced into a separator (known as a flash separator). The operation of expanding the mixture may take place with or preferably without the contribution of heat, i.e. under adiabatic conditions.

According to a variant of the invention, the water content in the partial vaporisation zone is kept at a value of at least 0.5% by weight with respect to the non-vaporised part. This can take place if need be by injection of water in said partial vaporisation zone, i.e. in the flash separator.

The vaporised part which comprises, amongst others, the produced acetic acid and/or methyl acetate may be placed in contact and washed in the upper part of the flash separator by a liquid coming from purification installations downstream.

Upon leaving the flash separator, the non-vaporised part which notably comprises the catalyst which has remained in solution, totally or partially, is recycled advantageously to the reactor, conventionally by means of a pump.

The vaporised part which further comprises the produced acetic acid and/or methyl acetate is then sent into a purification zone which comprises, usually, various distillation columns.

According to a variant of the invention, a supplementary placing in contact and washing may be carried out in the first distillation column with the aid of a liquid coming from the purification installations.

According to another variant of the invention, the reaction mixture, upon leaving the reactor, may be directly expanded in the first distillation column of the purification zone.

The various flows of separated material in the purification zone may be recycled towards the reactor or treated independently.

The acetic acid or methyl acetate obtained by this method is of sufficient quality to be sold without purification other than those known to the person skilled in the art and already in the public field.

The introduction of carbon monoxide may take place directly in the reactor, but also in the recycling zone of the non-vaporised liquid fraction, such that the carbon monoxide is not degasified directly towards the partial vaporisation zone of the reaction mixture. To this end, the introduction of carbon monoxide according to this latter possibility is more particularly carried out downstream from the reaction mixture recycling pump.

According to another variant of the invention, and with the aim of minimising the losses in carbon monoxide, the reaction mixture leaving the reactor in which the reaction according to the invention takes place, is introduced, before the partial vaporisation step, in a supplementary reactor. The result of this supplementary step is to consume the carbon monoxide dissolved in said reaction mixture in order to give the acid desired. From this, the losses in carbon monoxide during the partial vaporisation of the mixture are considerably limited.

The method of the invention, such as has been previously described and in all its variants, is most particularly applied to the preparation of acetic acid and/or methyl acetate from mixtures of methyl formate and methanol and, this, independent of the relative proportions of these two reagents.

Thus, the invention also relates to a method of preparation of acetic acid and/or methyl acetate by the reaction of methanol and methyl formate, in the presence of water, carbon monoxide, a solvent and a catalytic system comprising at least one halogenated promoter and at least one iridium-based compound, characterised in that a partial carbon monoxide pressure is kept between $0.1 \cdot 10^5$ Pa and $25 \cdot 10^5$ Pa, and an amount of methyl formate below 20% by weight of the reaction mixture.

The proportions of methyl formate and methanol may vary within a very large range. Generally, a weight ratio of methanol reagent to the methyl formate reagent will be chosen between 0.01 and 100 (included).

According to this method, the reaction system is characterised in the following way:
 the reagents are methyl formate, methanol and carbon monoxide;
 the catalytic system comprises iridium in a soluble form, and at least one promoter, advantageously methyl iodide;
 water;
 the solvent comprises acetic acid, formic acid and advantageously a co-solvent, methyl acetate.

According to a preferred embodiment of the method above, methyl formate and methanol are continuously fed into a reactor equipped with means of stirring.

Carbon monoxide of at least 98% purity is injected into the reactor in an adequate amount.

The temperature is advantageously kept at a value between 175° C. and 200° C.

The pressure is advantageously kept at a value between 20 and 30 absolute bars.

A gaseous flow is continuously extracted from the head of the reactor in order to maintain the partial carbon monoxide pressure at a value between 1 and 10 bars. It is treated and ridded of gaseous by-products of the reaction in a conventional section of treatment of gaseous vents.

The reaction mixture leaving the reactor is expanded in a flash separator. The non-vaporised part is recycled to the reactor by means of a pump. The vaporised part is sent into a purification zone which comprises various distillation columns.

The liquid flows originating from various purification zones and from the treatment of the gaseous vents and which comprise acetic acid, water, methanol, methyl formate, methyl acetate, iridium catalyst and its promoter methyl iodide, and formic acid are conventionally recycled towards the reactor.

The method is very selective and only generates few by-products. The principal by-products may be cited as illustration:
 gaseous: methane, carbon dioxide and hydrogen;
 and liquids: propionic acid.

Other by-products may be generated in small amounts and are removed according to the methods known to the person skilled in the art in the purification zone.

The acetic acid produced is of quality which is sufficient for it to be sold.

The ratio of starting materials feeding the reactor can vary in large proportions. Thus, in feeding the reactor with methyl formate of commercial quality which contains a few percent methanol, the consumption of carbon monoxide is low.

The acetic acid is produced principally by the isomerisation of methyl formate and in to a lesser extent by the carbonylation of methanol.

Another case of figure is to ensure a production supplement to a reaction system which consumes principally methanol and carbon monoxide. The contribution of methyl formate enables ensuring a diversification of the starting materials and generates an additional amount of acetic acid produced.

The weight ratio of methanol feeding the reactor to the methyl formate feeding the reactor can vary from 0.01 to 100.

Thus, this ratio is defined in terms of methanol reagent with respect to methyl formate reagent in the present text.

Concrete but non-limiting examples of the invention are now going to be presented.

EXAMPLE 1

Isomerisation and Carbonylation Reaction Without Recycling of the Catalyst

First of all, the catalytic solution is prepared as follows:
In an autoclave is introduced:
105 g of iridium iodide,
90 g of hydroiodic acid in 57% solution in water,
910 g of acetic acid.

The autoclave is then pressurised to $50 \cdot 10^5$ Pa (50 bar) of carbon monoxide.

The temperature is brought to 150° C.
The duration of the reaction is 4 hours.
The autoclave is then depressurised and then the reaction medium is cooled.

A red coloured solution is obtained which is decanted in order to obtain the catalytic solution.

In an autoclave in Hastelloy® B2, is introduced continuously a solution of iridium in acetic acid, prepared as above, acetic acid, methyl iodide, methyl formate, methanol and water.

The molar ratio of the methyl radicals fed in to the formyl radicals fed in is 2.4.

The composition of the reaction mixture under steady state conditions is the following:
water: 1.13%
methyl acetate: 25.8%
methyl iodide: 7.3%
formic acid: 13.0%
methyl formate: 17.7%
methanol: 0.29%
acetic acid: made up to 100%
the iridium concentration is: 3,080 ppm The partial carbon monoxide pressure is kept constant at a value of $10^5$ Pa (1 bar).

The total pressure upon leaving the reactor is $25 \cdot 10^5$ Pa (25 bar).

The temperature is kept at 190° C.±0.5° C.

The composition of the reaction mixture, in weight percent, given with a precision in the order of 2%, is determined by measurement by vapour phase chromatography.

The calculation of the rate of isomerisation is carried out on the liquid resulting from the reactor, cooled to ambient temperature and collected for a period of time between 30 and 60 minutes with respect to the flows of the compounds injected into the reactor during this same period, once the steady state conditions have been obtained.

The calculation of the rate of carbonylation is done following the gaseous evaluation on the consumed carbon monoxide.

A rate of isomerisation of 8 mol/h/l in acetic acid formed is obtained, and a rate of carbonylation of 11 mol/h/l in acetic acid formed. The acetic acid being in the form of acetic acid and methyl acetate.

EXAMPLE 2

Isomerisation Reaction with Carbonylation Reaction with Recycling of the Catalyst In an autoclave in Hastelloy® B2 containing catalyst prepared according to the method described in Example 1, the various components of the reaction mixture are injected continuously: acetic acid, methyl formate, methanol, methyl acetate, methyl iodide, and optionally water. The flows leaving the reactor are directed into a zone wherein a fraction containing the acetic acid produced is vaporised. The non-vaporised fraction containing the catalyst is recycled to the reactor. The vaporised fraction is condensed and represents the liquid effluents.

The composition of the reaction mixture under steady state conditions, determined by measurement, by vapour phase chromatography, of a sample taken from the reaction medium, expressed in weight percent, is the following:
water: 1.25%
methanol 0.15%
methyl acetate: 18.3%
methyl iodide: 9.7%
formic acid: 5.9%
methyl formate: 3.0%
acetic acid: made up to 100%
the iridium concentration is: 2,180 ppm The temperature is kept at 190° C.+/−0.5° C.

The total pressure of the reaction is kept at 2.4 MPa+/−20kPa (24 bar).

The partial carbon monoxide pressure is kept constant at a value of 1.05 MPa (10.5 bar); the purity of the CO used is greater than 99%.

The calculation of the rate of acetic acid formation by both the reactions of isomerisation of methyl formate and carbonylation of methanol is carried out using an evaluation of the liquid effluents from the vaporisation zone collected during a given period (between 2 and 4 hours), with respect to the flow of the compounds injected in the same time lapse, once steady state conditions have been reached. The calculation of the rate of carbonylation is done following the gaseous evaluation on the carbon monoxide consumed.

An isomerisation rate of 1.2 $mol.h^{-1}.l^{-1}$ in acetic acid formed is obtained, and a carbonylation rate of 15.7 $mol.h^{-1}.l^{-1}$ in acetic acid formed. The acetic acid is in the form of acetic acid and methyl acetate.

The molar ratio of the methyl radicals fed in to the formyl radicals fed in is 14.1.

What is claimed is:

1. Method of preparing at least one compound selected from the group consisting of acetic acid and methyl acetate by simultaneous isomerization and carbonylation, comprising reacting at least one reagent which provides formyl radicals and at least one further reagent which provides methyl radicals, in a reaction mixture containing water, carbon monoxide, a solvent and a catalytic system comprising at least one halogenated promoter and at least one iridium-based compound, wherein the carbon monoxide is maintained in the reaction mixture at a partial pressure between $0.1 \cdot 10^5$ Pa and $25 \cdot 10^5$ Pa, the at least one reagent which provides the formyl radicals is kept below or equal to 20% by weight of the reaction mixture, the at least one reagent which provides the methyl radicals and the at least one reagent which provides the formyl radicals are fed into the mixture so as to provide a molar ratio of methyl radicals to formyl radicals of greater than 1 and water is maintained in the reaction mixture in a non-zero amount which is at most 5% by weight of the reaction mixture.

2. Method according to claim 1, wherein said reagent which provides formyl radicals is a compound of formula HC(O)OR, in which R represents a hydrogen atom or a methyl group.

3. Method according to claim 1 wherein said reagent which provides methyl radicals is of formula $CH_3$—R', in which formula —R' represents —OH, —$OCH_3$, —OC(O)$CH_3$, —OC(O)H and mixtures thereof.

4. Method according to claim 1, wherein the reaction is carried out with a molar ratio of the methyl radicals to the formyl radicals of between 1 (excluded) and 100.

5. Method of preparing at least one compound selected from the group consisting of acetic acid and methyl acetate comprising carbonylation of methanol and isomerization of methyl formate, in a reaction mixture containing water, carbon monoxide, a solvent and a catalytic system comprising at least one halogenated promoter and at least one iridium-based compound, wherein the carbon monoxide is maintained in the reaction mixture at a partial pressure between $0.1 \cdot 10^5$ Pa and $25 \cdot 10^5$ Pa, methyl formate is kept below 20% by weight of the reaction mixture and water is maintained in the reaction mixture in a non-zero amount which is at most 5% by weight of the reaction mixture.

6. Method according to claim 5, wherein the reaction is carried out with a weight ratio of methanol feeding the reaction mixture to the methyl formate reagent feeding the reaction mixture of between 0.01 and 100 (included).

7. Method according to claim 1, wherein the partial carbon monoxide pressure is maintained at greater than $0.5 \times 10^5$ Pa.

8. Method according to claim 1, wherein the partial carbon monoxide pressure is maintained lower than or equal to $15 \times 10^5$ Pa.

9. Method according to claim 1, wherein the halogenated promoter in the reaction mixture is maintained between 0.1 and 20% by weight.

10. Method according to claim 1, wherein the reaction is carried out in the presence of a solvent which is selected from the group consisting of aliphatic carboxylic acids having 2 to 10 carbon atoms.

11. Method according to claim 1, wherein the reaction is carried out in the presence of formic acid at a content kept below 15% by weight of the reaction mixture.

12. Method according to claim 12, characterised in that the formic acid content is kept below 10% by weight of the reaction mixture.

13. Method according to claim 11, wherein the reaction mixture contains more than 25% by weight of free carboxylic acids.

14. Method according to claim 1, wherein the reaction is carried out in the presence of a co-solvent which is methyl acetate.

15. Method according to claim 15, wherein the weight content of the co-solvent in the reaction mixture is lower than or equal to that of acetic acid.

16. Method according to claim 1, wherein the reaction is carried out in the presence of a halogenated promoter selected from the group consisting of iodinated compounds and precursors of such compounds.

17. Method according to claim 1, wherein the reaction is carried out continuously.

18. Method according to claim 5, wherein the partial carbon monoxide pressure is maintained greater than or equal to $0.5 \cdot 10^5$ Pa.

19. Method according to claim 5, wherein the partial carbon monoxide pressure is maintained lower than or equal to $15 \cdot 10^5$ Pa.

20. Method according to claim 5, wherein the halogenated promoter in the reaction mixture is maintained between 0.1 and 20% by weight.

21. Method according to claim 5, wherein the reaction is carried out in the presence of a solvent which is selected from the group consisting of aliphatic carboxylic acids having 2 to 10 carbon atoms.

22. Method according to claim 5, wherein the solvent comprises formic acid at a content below 15% by weight of the reaction mixture.

23. Method according to claim 21, wherein the reaction mixture contains more than 25% by weight of free carboxylic acids.

24. Method according to claim 5, wherein the reaction is carried out in the presence of a co-solvent which is methyl acetate.

25. Method according to claim 5, wherein the reaction is carried out in the presence of a halogenated promoter selected from the group consisting of iodinated compounds and precursors of such compounds.

26. Method according to claim 5, wherein the reaction is carried out continuously.

27. Method according to claim 1, wherein the water is maintained in an amount which is at most 2% by weight of the reaction mixture.

28. Method according to claim 1, wherein the partial pressure of carbon monoxide is less than or equal to $10 \cdot 10^5$ Pa.

29. Method according to claim 5, wherein the water is maintained in an amount which is at most 2% by weight of the reaction mixture.

30. Method according to claim 5, wherein the partial pressure of carbon monoxide is less than or equal to $10 \cdot 10^5$ Pa.

31. Method according to claim 24, wherein the formic acid content is kept below 10% by weight of the reaction mixture.

32. Method according to claim 26, wherein the weight content of said co-solvent in the reaction mixture is lower than or equal to that of acetic acid.

* * * * *

UNITED STATES PATENT AND TRADEMARK OFFICE
CERTIFICATE OF CORRECTION

PATENT NO.     : 6,395,927 B1
DATED          : May 28, 2002
INVENTOR(S)    : Carl Patois et al.

It is certified that error appears in the above-identified patent and that said Letters Patent is hereby corrected as shown below:

<u>Column 2,</u>
Line 64, change "alogenated" to -- halogenated --.

<u>Column 3,</u>
Line 28, change "iridiumbased" to -- iridium-based --.

<u>Column 10,</u>
Lines 58-59, change "$mol.h^-1.l^{-1}$" to -- $mol.h^{-1}l^{-1}$ --

<u>Column 11,</u>
Line 61, change "12" to -- 11 --.

<u>Column 12,</u>
Line 1, change "11" to -- 10 --.
Line 7, change "15" to -- 14 --.
Line 56, change "24" to -- 22 --.
Line 61, change "26" to -- 24 --.

Signed and Sealed this

Twentieth Day of May, 2003

JAMES E. ROGAN
*Director of the United States Patent and Trademark Office*